(12) United States Patent
Witt et al.

(10) Patent No.: US 9,575,105 B1
(45) Date of Patent: Feb. 21, 2017

(54) SYSTEMS AND METHODS FOR LOW POWER TIME-DOMAIN MEASUREMENT OF COMPLEX IMPEDANCE

(71) Applicant: Maxim Integrated Products, Inc., San Jose, CA (US)

(72) Inventors: Kevin James Witt, Colorado Springs, CO (US); John Fisher Di Cristina, Acton, MA (US)

(73) Assignee: Maxim Integrated Products, Inc., San Jose, CA (US)

( * ) Notice: Subject to any disclaimer, the term of this patent is extended or adjusted under 35 U.S.C. 154(b) by 266 days.

(21) Appl. No.: 14/496,516

(22) Filed: Sep. 25, 2014

Related U.S. Application Data

(60) Provisional application No. 62/017,050, filed on Jun. 25, 2014.

(51) Int. Cl.
*A61B 5/05* (2006.01)
*G01R 27/28* (2006.01)
*G01R 27/16* (2006.01)

(52) U.S. Cl.
CPC .................. *G01R 27/16* (2013.01)

(58) Field of Classification Search
USPC ............... 324/607, 649, 663, 681–690, 71.1
See application file for complete search history.

(56) References Cited

U.S. PATENT DOCUMENTS

| | | | | |
|---|---|---|---|---|
| 5,807,272 A | * | 9/1998 | Kun | A61B 5/0537 600/547 |
| 6,970,738 B1 | * | 11/2005 | Othman | A61B 5/053 600/547 |
| 2011/0115499 A1 | * | 5/2011 | Chodavarapu | G01R 27/26 324/649 |

* cited by examiner

*Primary Examiner* — Vincent Q Nguyen
(74) *Attorney, Agent, or Firm* — North Weber & Baugh LLP

(57) ABSTRACT

Various embodiments of the invention enable low-power accurate measurement of complex impedance at a range of frequencies of interest to determine a frequency response of a test sample. The system requires only a few external precision components that are not integrated into a microprocessor, thereby, providing a low-cost alternative to existing designs. In certain embodiments, low-power operation is accomplished by utilizing a simplified digital signal processing scheme that requires only a small number of ADC samples. Measurement accuracy is achieved by a digital conversion to baseband that does not suffer from channel matching issues and by utilizing a single analog path.

10 Claims, 5 Drawing Sheets

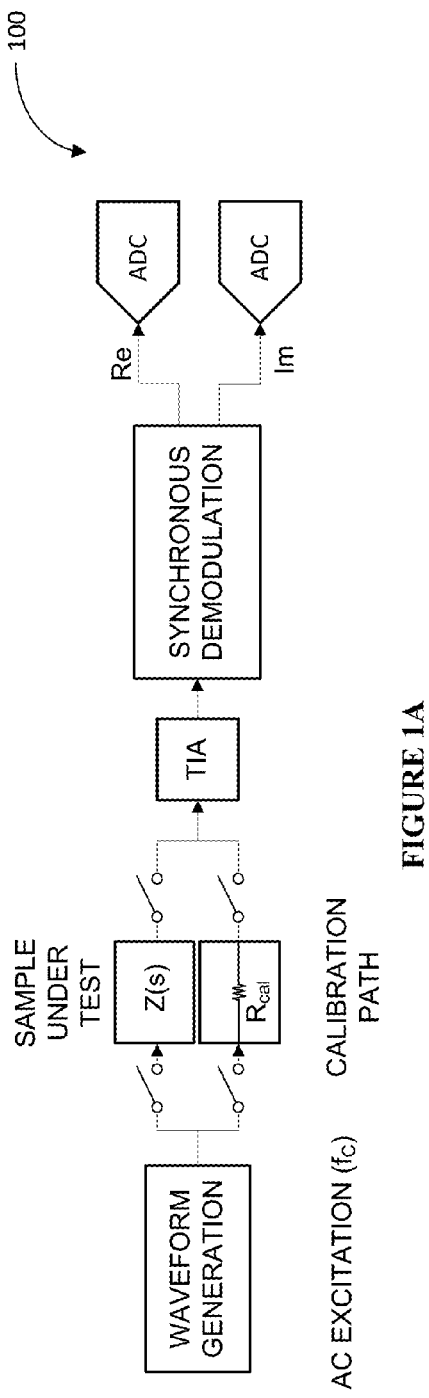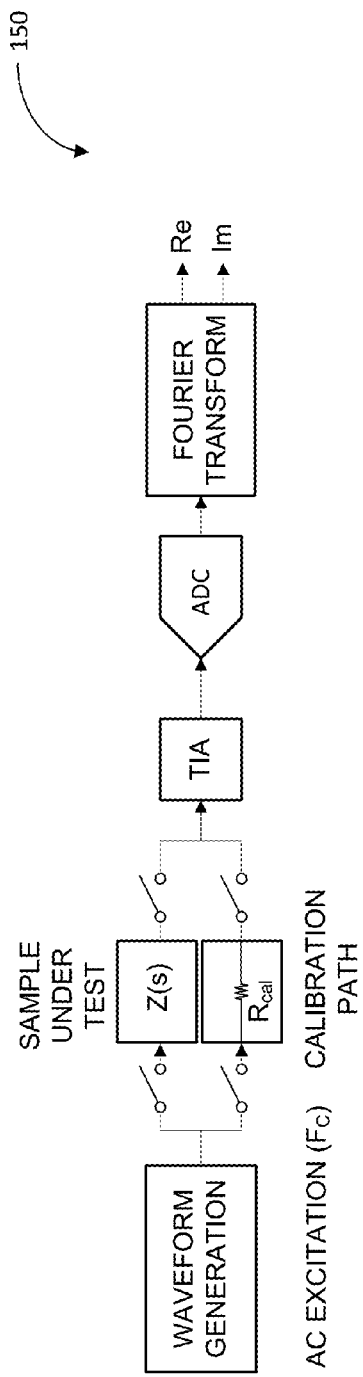
FIGURE 1A
PRIOR ART
FIGURE 1B
PRIOR ART

SYSTEMS AND METHODS FOR LOW POWER TIME-DOMAIN MEASUREMENT OF COMPLEX IMPEDANCE

CROSS REFERENCE TO RELATED PATENT APPLICATIONS

This application is related to and claims the priority benefit of and commonly-assigned U.S. Patent Application Ser. No. 62/017,050, filed on Jun. 25, 2014, titled "System and Method for Low Power Time-Domain Measurement of Complex Impedance," listing inventors Kevin Witt and John Di Cristina, which application is herein incorporated by reference in its entirety.

BACKGROUND

A. Technical Field

The present invention relates to the field of measuring network responses in the time-domain and, more particularly, to systems, devices, and methods of measuring complex impedance of test samples, including biomedical test samples.

B. Background of the Invention

A number of instruments in the biomedical and fitness area, such as blood glucose meters, respiration monitors, and galvanic skin response meters are designed to measure impedance or conductance of a biological sample in order to generate diagnostic and other useful information. By measuring the AC impedance of a person's skin, for example, a galvanic skin response can be obtained from which an estimate of a person's hydration level may be made.

More complicated devices that, for example, measure the impedance of a blood sample on a blood glucose measurement strip that contains chemicals require enhanced accuracy and perform relatively complicated AC impedance measurements from which diagnostic information may then be extracted. Some existing methods utilize an analog down-conversion process that necessitates a relatively high number of circuit components. However, this process is prone to channel mismatch and low accuracy caused by gain mismatch issues.

Other existing approaches apply Fast Fourier Transform (FFT) methods which utilize a rather power-hungry conversion process to feed large amounts of data samples through an analog-to-digital converter followed by a sophisticated post-processing algorithm. From the system response a transfer function is then calculated in order to extract magnitude and phase information from which then the complex impedance of a test sample is determined.

With the advent of portable electronics, however, the demand for lower power portable medical instrumentation with extended battery life is becoming increasingly important. Unfortunately, the high price of accuracy paid in the form of complicated circuitry that requires relatively high power and operates with inefficient algorithms is incompatible with the goal of modern portable and wearable instruments. What is needed are systems and methods to overcome the above-described limitations.

SUMMARY OF THE INVENTION

The disclosed systems and methods provide for a low power approach to measure a network response in the time-domain and accurately determine the complex impedance of any biometric test load at a given frequency. In particular, in various embodiments of the invention direct digital waveform synthesis is combined with a simplified analog test circuit and coherent digital baseband quadrature sampling to determine the complex impedance of the test load (e.g., skin, tissue, reactive test material).

In certain embodiments, a testing circuit, which may be used as a capacitive to digital converter, is stimulated by a coherent sinusoidal input signal and a network response is coherently detected by a digital baseband quadrature sampling receiver that extracts both amplitude and phase information of the network response from which the complex impedance can be easily determined.

Circuit responses of the testing circuit combined with measurements on a known calibration channel allow for the determination of the complex impedance for a testing sample at the desired testing frequency. To determine the response of a channel containing the test load and the calibration channel, a minimum of only two ADC samples is required. The simplified digital processing greatly reduces power consumption. The SNR of the estimate can be enhanced by averaging the impedance estimates in exchange for a slight increase in power consumption. In one embodiment, the test load is used as part of the input impedance of an inverting operational amplifier circuit that serves as a low-pass filter.

In addition, the test circuit supports calibration of frequency-dependent components to improve accuracy with only a small number of precision components. In order to accurately determine a broad range of AC impedances, i.e., the complex impedance of the circuit response as a function of frequency, the complex impedance may be measured at a series of discrete frequencies.

BRIEF DESCRIPTION OF THE DRAWINGS

Reference will be made to embodiments of the invention, examples of which may be illustrated in the accompanying figures. These figures are intended to be illustrative, not limiting. Although the invention is generally described in the context of these embodiments, it should be understood that this is not intended to limit the scope of the invention to these particular embodiments.

FIG. 1A is a prior art circuit to measure complex impedance using an analog down-conversion process.

FIG. 1B is a prior art circuit to measure complex impedance using FFT.

DETAILED DESCRIPTION OF THE PREFERRED EMBODIMENTS

In the following description, for the purpose of explanation, specific details are set forth in order to provide an understanding of the invention. It will be apparent, however, to one skilled in the art that the invention can be practiced without these details. One skilled in the art will recognize that embodiments of the present invention, described below, may be performed in a variety of ways and using a variety of means. Those skilled in the art will also recognize that additional modifications, applications, and embodiments are within the scope thereof, as are additional fields in which the invention may provide utility. Accordingly, the embodiments described below are illustrative of specific embodiments of the invention and are meant to avoid obscuring the invention.

Reference in the specification to "one embodiment" or "an embodiment" means that a particular feature, structure, characteristic, or function described in connection with the embodiment is included in at least one embodiment of the invention. The appearance of the phrase "in one embodiment," "in an embodiment," or the like in various places in the specification are not necessarily referring to the same embodiment.

Furthermore, connections between components or between method steps in the figures are not restricted to connections that are affected directly. Instead, connections illustrated in the figures between components or method steps may be modified or otherwise changed through the addition thereto of intermediary components or method steps, without departing from the teachings of the present invention.

In this document "sample under test," "device under test," "test load," and "DUT" are used interchangeably and includes skin samples and other test loads recognized by one of skilled in the art.

FIG. 1A is a prior art circuit to measure complex impedance using an analog down-conversion process. In order to determine the complex impedance of the test sample, this circuit applies a sinusoidal waveform to the test sample and a calibration path and utilizes a transimpedance amplifier and synchronous demodulation to extract real and imaginary parts of the system response via analog-to-digital-converters. Major drawbacks of this approach are the high number of required circuit components and the overall low accuracy of the system due to channel mismatch. FIG. 1B is a prior art circuit to measure complex impedance using fast fourier transformation. This design applies a large number of data points to the ADC and an elaborate post-processing conversion algorithm in order to determine the complex impedance of the test sample, which negatively impacts the power efficiency of the circuit.

Therefore, it would be desirable to have tools that would allow designers to determine the complex impedance of test samples accurately and efficiently while significantly reducing power consumption.

Figure 2:
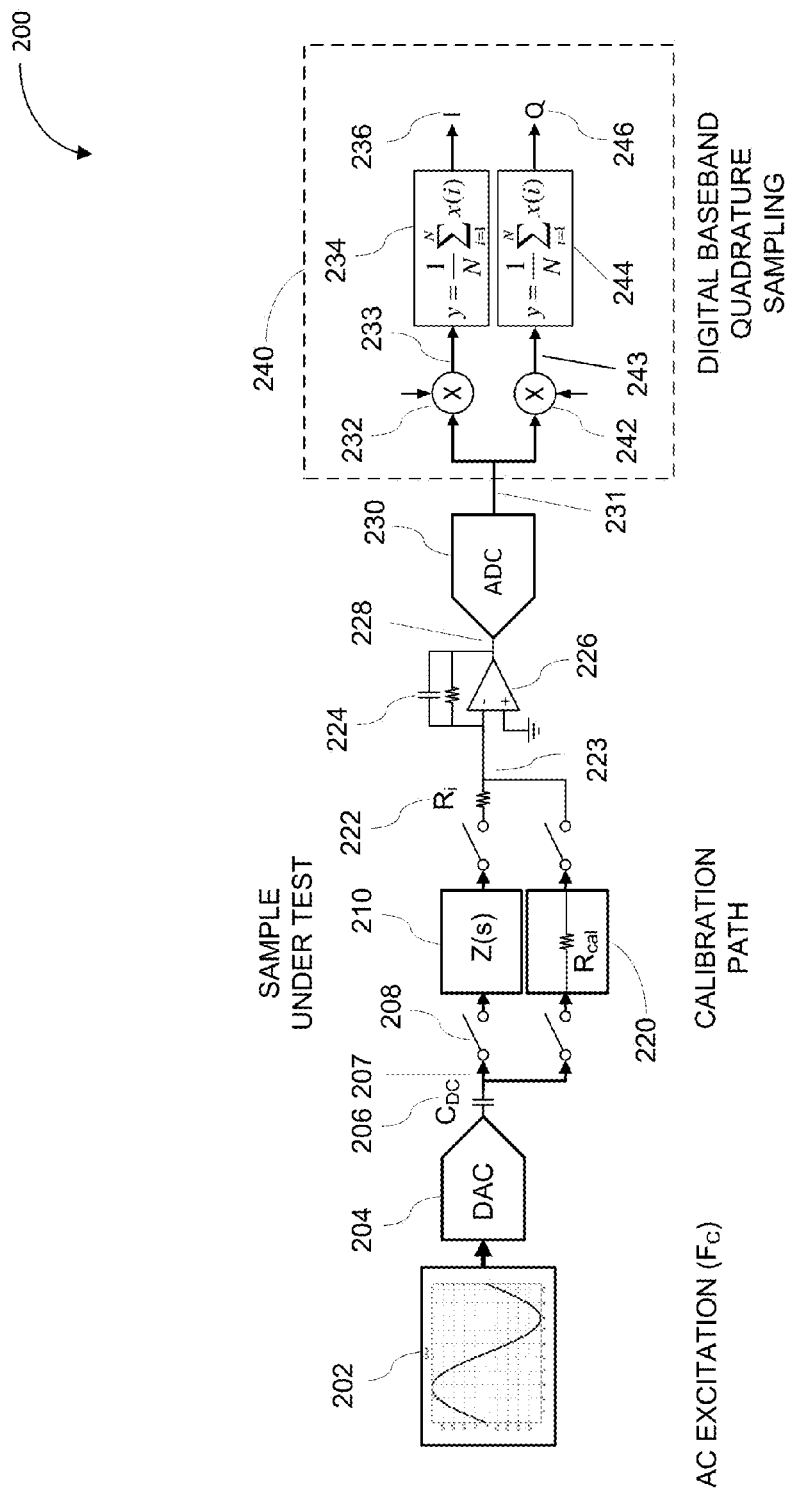
FIG. 2 is a schematic of an exemplary circuit to measure complex impedance in the time-domain, according to various environment of the invention.

FIG. 2 illustrates an exemplary circuit to measure impedance in the time-domain. Circuit 200 comprises a digital representation of an AC excitation 202 that provides a stimulus to digital-to-analog converter (DAC) 204, DC blocking capacitor 206, sample under test (DUT) 210, calibration resistor 220, input resistor 222, operational amplifier circuit 226, which further comprises a parallel combination of a resistor and a capacitor in its feedback path 224, analog-to-digital converter (ADC) 230, and digital baseband quadrature sampling receiver circuit 240. In this example, receiver circuit 240 comprises multiplier 232, 242 and averaging means 234, 244.

DAC 204, together with a DMA-based circular buffer (not shown), produces a waveform signal at a desired frequency, e.g., a sinusoidal waveform. Potential DC voltages are removed from the waveform by blocking capacitor 206 before the signal is passed through sample under test 210 into inverting operational amplifier circuit 226. The DC-free waveform signal is selectively input into sample under test 210 in a measurement path and into a calibration resistor 220 in a calibration path via a combination of switches 208 that isolate the calibration path from the measurement path. In this example, operational amplifier circuit 226 low-pass filters signal 223 that is then input to ADC 230 for digital conversion. As shown in FIG. 2, digital output signal 231 of ADC 230 undergoes digital signal processing provided by baseband quadrature sampling. Digital baseband quadrature sampling receiver 240 applies a down-conversion process to digital signal 231. The process measures the amplitude and phase of the system response of system 200.

In detail, the real and imaginary parts, I 236 and Q 246 of the network response, are measured for measurement path 210 and, in no particular order, the process is repeated by routing analog signal 207 through calibration path 220. In this manner, the signal path terms common to both paths 210, 220 can be calibrated out, which greatly simplifies the calculation of the complex impedance, Z, of DUT 210. From the ratio of the network responses of DUT 210 and calibration path 220 Z can be accurately determined. In order to determine the response of each path 210, 220 a minimum of only two ADC samples 231 is required. As a result, by using coherent direct digital sinusoidal modulation and digital baseband quadrature sampling receiver 240, the complex impedance of test load 210 can be determined from a low power measurement. It is understood that the system accuracy can be increased by averaging an appropriate number of samples of signal 228.

In one embodiment, as will be discussed with respect to FIG. 3, signal processing and test configuration may be provided by a microprocessor. Further, timing and control logic is used to enable the synchronization of the DAC-based digital waveform generation with the ADC sampling. It is noted that the present invention is not limited to biomedical applications, as industrial and other applications may also benefit from the systems and methods that provide for low-power impedance measurement as described herein.

Figure 3:
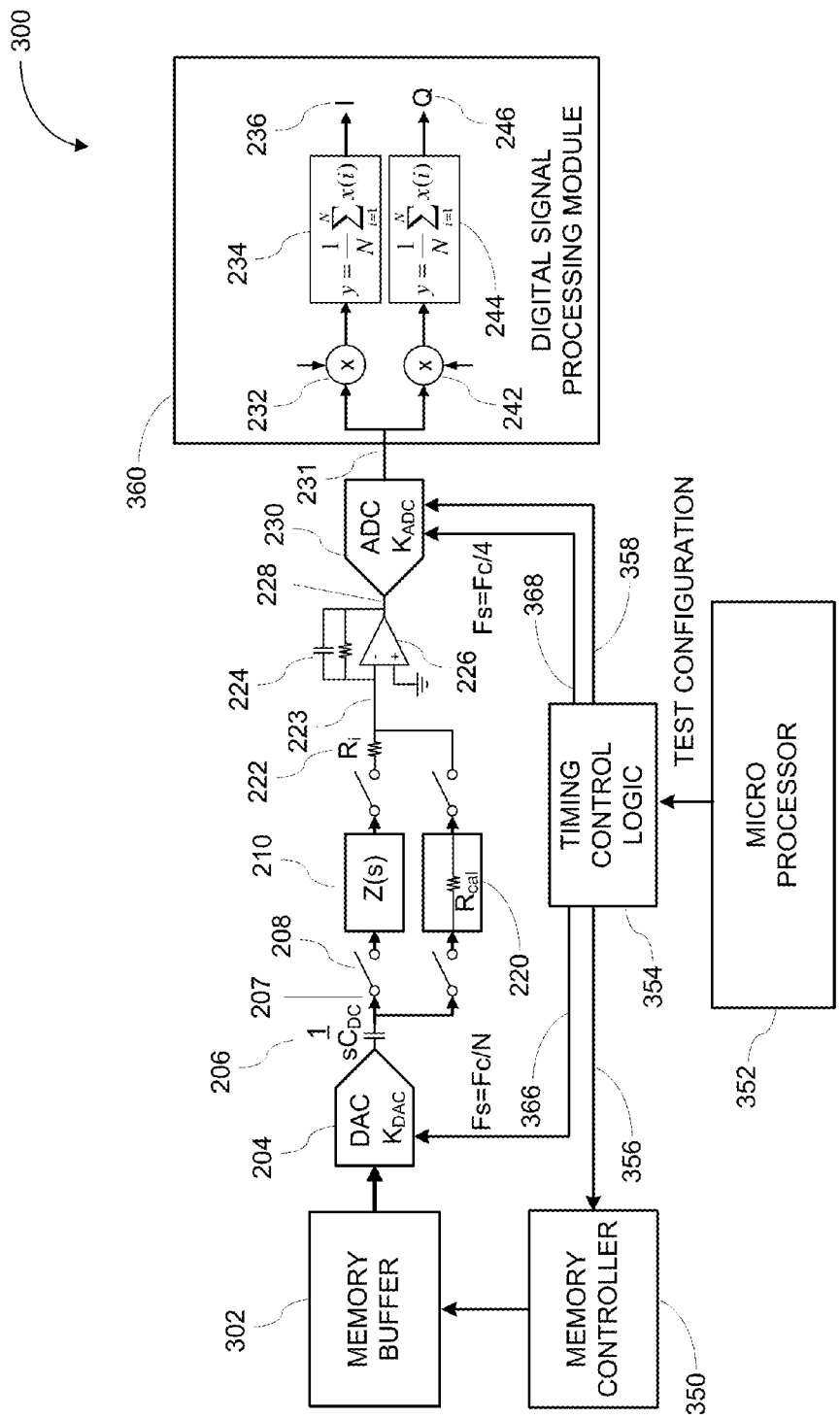
FIG. 3 is a schematic of an exemplary system to measure complex impedance in the time-domain, according to various embodiments of the invention.

FIG. 3 illustrates an exemplary system to measure impedance in the time-domain. Components similar to those shown in FIG. 2 are labeled in the same manner. For purposes of brevity, a description or their function is not repeated here. In example in FIG. 3, circuit 300 comprises memory buffer 302, which may be a circular buffer that is controlled by memory controller 350, DAC 204, blocking capacitor 206, DUT 210, calibration resistor 220, operational amplifier circuit 226, ADC 230, digital signal processing module 240, which further comprises multiplier 232, 242 and averaging means 234, 244, timing control logic 354, and microprocessor 352.

In operation, memory controller 350 acts as an address generator for memory buffer 302 and retrieves digital waveform data to be output by DAC 204. In response to receiving data from memory buffer 302, DAC 204 outputs waveform signals, e.g., a sinusoidal excitation signal at a certain generation rate $f_C$ creating a direct digital synthesis module. The output rate of DAC 204 determines the frequency of the waveform, such that by adjusting the output rate the frequency of waveform signal 207 can be controlled. Switches 208 selectively pass the waveform data through sample under test 210 and calibration resistor 220 into operational amplifier circuit 226 and further into ADC 230. In one embodiment, the waveform is compensated, for example, by a pre-distortion calibration, in order to account for non-idealities in circuit components such as DAC 204, LPF 226 or ADC 230.

Timing control logic 354 comprises a timing generator that generates a clock signal 366. One of ordinary skill in the art will appreciate that timing control logic 354 may comprise other components, such as a state machine, not discussed herein for purposes of brevity. Timing control logic 354 also generates control signals that control both DAC 204 and ADC 230. In response to clock signal 366, control signals 356 cause DAC 204 to start a digital-to-analog conversion that generates the waveform data at an output rate of Fc/N. Simultaneously, or with some time delay, ADC 230 collects data at a sample rate of Fc/4.

In one embodiment, the clock ensures that control signals 356, 358 synchronize the digital waveform generation by DAC 204 with the data collection and the sampling process by ADC 230. For example, the digital-to-analog conversion may be started at a certain phase of a sine wave (e.g., zero phase) in order to begin the modulation and, simultaneously, the analog-to-digital conversion by ADC 230 is triggered to ensure control over the exact starting phase each time a measurement is performed. This synchronizes the phase of data capture with the phase of data generation. The importance of coherent timing control will become apparent from a more detailed explanation of the operation of system 300.

In order to measure complex impedance at a desired frequency, Fc, a sinusoidal voltage $x(t)=\cos(2\pi F_c \cdot t)$ is applied to test load 210. Signal 228 $y(t)=V_L \cos(2\pi F_c \cdot t + \theta)$ received by ADC 230 is a scaled and phase shifted version of input signal 207. In one embodiment, to extract phase information from received signal 228, coherent detection is applied as follows. Digital Baseband Quadrature Sampling (BQS), which is a digital down-conversion to DC, is implemented to synchronize ADC sampling with AC waveform generation. For this purpose, ADC 230 is sampled with the same start signal and clock signal that provides timing for the sample rate such that signal 228 can be sampled at a rate that is a multiple of the generation frequency. Digital BQS is typically illustrated in the frequency domain but for AC impedance measurements the time domain analysis is more applicable. For a sinusoidal waveform, in one embodiment, the ADC 230 discretizes a cosine waveform by sampling the waveform at four equidistant intervals per period, i.e., with a sampling frequency of ADC 230 that is four times higher than the frequency generated by DAC 204.

The following equations illustrate the process to extract the real and imaginary components, i.e., respective signals I 236 and Q 246 from analog signal 228.

$$y(k) = V_L \cos(2\pi F_c \cdot kT_s + \theta)$$

$$T_s = \frac{1}{4F_c}$$

$$y(k) = V_L \cos\left(\frac{\pi}{2}k + \theta\right)$$

$$k \in \{0,1,2, \ldots N-1\}$$

$$y(k) = V_L\left(\cos(\theta) \quad \cos\left(\frac{\pi}{2}+\theta\right) \quad \cos(\pi+\theta) \quad \cos\left(\frac{3\pi}{2}+\theta\right) \ldots\right)$$

$$y(k) = V_L(\cos(\theta) - \sin(\theta) - \cos(\theta)\sin(\theta) \ldots)$$

Figure 4:
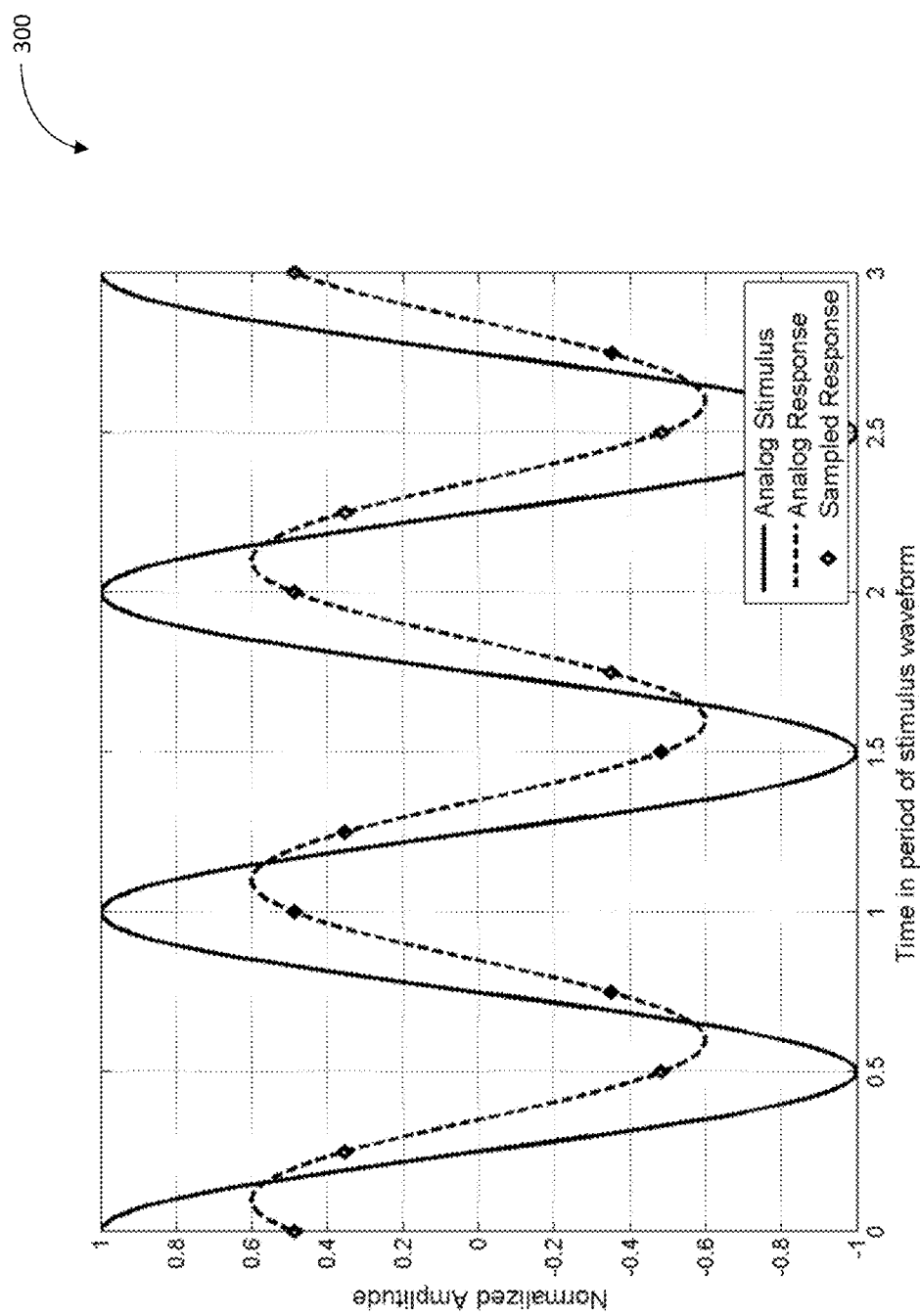
FIG. 4 illustrates sampling applied to an exemplary sinusoidal waveform according to various embodiments of the invention.

This temporal result is apparent upon closer examination of FIG. 4. We are interested in extracting the magnitude and phase information.

$$V_L e^{j\theta} = V_L \cos(\theta) + jV_L \sin(\theta) = I + jQ$$

By observation, the first two ADC samples y(0) and −y(1) already yield I 236 and Q 246.

$$I = V_L \cos(\theta) = y(0)$$

$$Q = V_L \sin(\theta) = -y(1)$$

ADC samples 231 can be split into even and odd and can be modulated by +/−1 in order to generate multiple observations of I 236 and Q 246. As a result, measuring a minimum of two samples is sufficient to compute I 236 and Q 246. In contrast to existing designs that measure 1024 data points and apply a cumbersome FFT process, this novel approach significantly reduces the power requirements imposed on system 300.

In one embodiment, at a given frequency at which the data is being processed, output signal 231 may be averaged, as illustrated below, to obtain an increased signal-to-noise ratio of the measurement signal.

$$I = \frac{2}{N+1} \sum_{i=0}^{\frac{N+1}{2}-1} y(2i)(-1)^i$$

$$Q = \frac{2}{N+1} \sum_{i=0}^{\frac{N+1}{2}-1} y(2i+1)(-1)^{i+1}$$

$$\text{Phase} = \theta = a\tan 2(Q,I)$$

$$\text{Magnitude} = V_L = \sqrt{I^2 + Q^2}$$

I 236 and Q 246 are determined for measurement path 210, which sets the relative phase, so that when switch 208 is set to measure calibration path 220 all components in calibration path 220 are measured relative to measurement path 210. Thus, a repeatable and coherent process calibrates out any effects of DAC 204, AC blocking capacitor 206, operational amplifier 224, and ADC 230, so that the only non-common elements in the two paths are external calibration resistor, $R_i$ 222, and switches 208, which have an on resistance that contributes only minimally to differences in the two paths, as it is relatively small in comparison with other resistances in system 300. Similarly, circuit delays may be calibrated out.

Once the magnitude and phase data, i.e., I 236 and Q 246, are extracted for calibration load 220 and sample under test 210, the complex impedance, Z(s), can be estimated from the complex system responses $Y_{CAL}(s)$ of calibration load 220 and $Y_{SYS}(s)$ of sample under test 210 at the frequency of interest. Based on the ratio of the responses and the two external resistors $R_i$ 222 and $R_{CAL}$ 220, the impedance at the test frequency, Z(s), can be derived by accounting for external precision calibration resistors $R_i$ 222 and $R_{CAL}$ 220 as follows:

$$Y_{cal}(s) = \frac{K_{dac}K_{adc}}{sC_{dc}}\left(\frac{-R_{fb}/R_{cal}}{sR_{fb}C_{fb}+1}\right)X(s)$$

$$Y_{sys}(s) = \frac{K_{dac}K_{adc}}{sC_{dc}}\left(\frac{-R_{fb}/(Z(s)+R_i)}{sR_{fb}C_{fb}+1}\right)X(s)$$

$$\frac{Y_{cal}(s)}{Y_{sys}(s)} = \frac{1/R_{cal}}{1/(Z(s)+R_i)} = \frac{Z(s)+R_i}{R_{cal}}$$

$$Z(s) = R_{cal}\frac{Y_{cal}(s)}{Y_{sys}(s)} - R_i$$

Advantageously, since the measurement involves ratios, all common path components drop out from the impedance equation, i.e., they are calibrated out of the impedance estimation. In short, after measuring I 236 and Q 246 and determining the complex system responses, microprocessor 352 multiplies their ratio by the value of calibration resistor 220 and subtracts the value of resistor 222 to arrive at Z(s).

In one embodiment, digital signal processing is provided by microprocessor 352 into which timing control logic 354 may be implemented. The only external components other than sample under test 210 are the passive components, including DC blocking cap 206, calibration resistor 220, and components in the feedback path 224 of operational amplifier circuit 226. The only precision components, in example in FIG. 3, are external resistors $R_i$ 222 and $R_{CAL}$ 220. In one embodiment, resistor $R_i$ 222 is optionally based on the impedance of sample under test 210 and is used to increase the robustness of system 300 to a wider range of external test loads 210.

Based on the complex impedance observation, for example, the capacitance of a purely capacitive test load 210, Z(s)=1/sC, can be determined from equation $$C = \frac{1}{2\pi F_c |\text{Im}(Z(s))|}$$

It is noted that the sampling rate is not intended as a limitation on the scope of the invention as other sampling rates (e.g., 64 samples per cycle) are possible.

Figure 5:
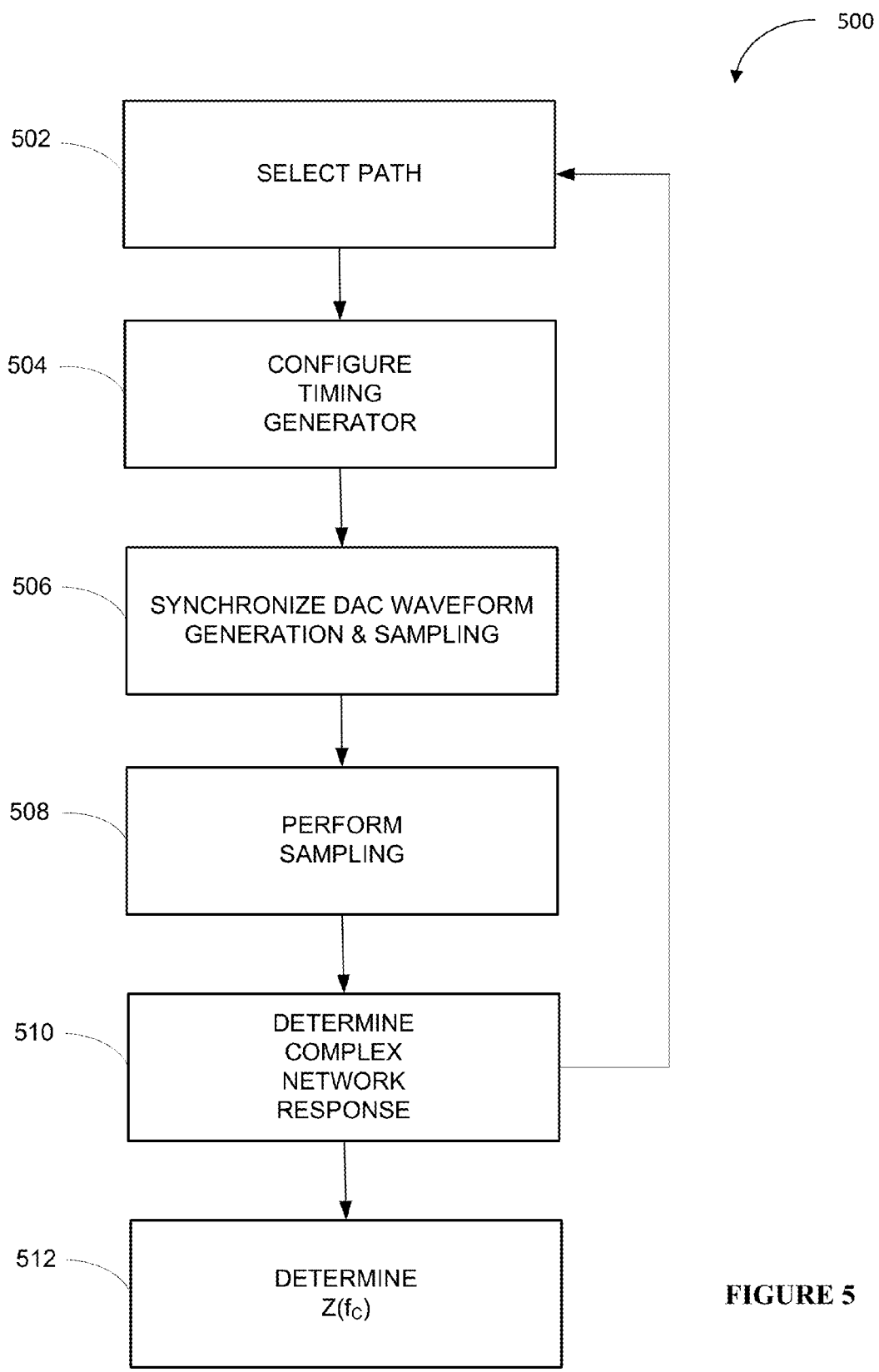
FIG. 5 is a flowchart of an illustrative process for measuring impedance in the time-domain in accordance with various embodiments of the invention.

FIG. 5 is a flowchart of an illustrative process for measuring complex impedance in the time-domain in accordance with various embodiments of the invention. Process 500 for measuring the impedance of a sample under test starts at step 502 when one of two paths, a measurement and a calibration path is selected. The measurement path comprises the sample under test to be measured. The calibration path comprises a calibration resistor.

At step 504, a timing generator is configured, for example, to generate clock and control signals that control output and sample rates of a DAC and an ADC at a given frequency.

At step 506, a digital-to-analog conversion that generates a digital waveform is synchronized with analog-to-digital sampling, e.g., by simultaneously starting waveform generation and sampling process.

At step 508, data sampling is performed, for example, by an ADC that samples a certain number of data points on a sinusoidal waveform.

At step 510, a complex network response for the selected path is determined from the sampled data, and the process is repeated for a previously not selected path, e.g., by switching between the paths via a switching network.

Finally, at step 512, the complex network responses are used to calculate a complex impedance as a function of frequency.

It will be appreciated by those skilled in the art that fewer or additional steps may be incorporated with the steps illustrated herein without departing from the scope of the invention. No particular order is implied by the arrangement of blocks within the flowchart or the description herein.

It will be further appreciated that the preceding examples and embodiments are exemplary and are for the purposes of clarity and understanding and not limiting to the scope of the present invention. It is intended that all permutations, enhancements, equivalents, combinations, and improvements thereto that are apparent to those skilled in the art, upon a reading of the specification and a study of the drawings, are included within the scope of the present invention. It is therefore intended that the claims include all such modifications, permutations, and equivalents as fall within the true spirit and scope of the present invention.

We claim:

1. A circuit to measure impedance in the time domain, the circuit comprising:
    an analog input signal generator that generates an analog input signal;
    a measurement path that comprises a device under test and generates a measurement signal in response to the analog input signal;
    a calibration path that generates a calibration signal in response to the analog input signal;
    a sampling circuit selectively coupled to the measurement path and the calibration path to generate respective first and second circuit responses;
    a clock signal to synchronize a start of the analog input signal generation with the at least one of the measurement signal and the calibration signal; and
    a digital baseband quadrature sampling receiver coupled to the sampling circuit, the digital baseband quadrature sampling receiver down-converts the first and second circuit responses to generate a quadrature signal that comprises in-phase and quadrature components and eliminates terms associated with path components common to the first and second response to determine a complex impedance for the device under test at a predetermined testing frequency.

2. The circuit according to claim 1, wherein the analog input signal is created by a DAC from a sinusoidal digital input waveform.

3. The circuit according to claim 2, further comprising a DMA-based circular buffer and a memory controller that are coupled to the DAC to generate the sinusoidal digital input waveform having an adjustable frequency.

4. The circuit according to claim 1, wherein the digital baseband quadrature sampling receiver determined the complex impedance from a ratio of the first and second circuit responses.

5. The circuit according to claim 1, further comprising a timing logic and a control logic that generate the clock signal and enable a synchronization of the analog input signal and the measurement signal.

6. The circuit according to claim 1, wherein the clock signal is configured to synchronize phases of data capture and data generation.

7. The circuit according to claim 1, further comprising a pre-distortion calibration circuit that is configured to compensate for circuit non-idealities.

8. The circuit according to claim 1, further comprising a switching network that isolates the measurement path from the calibration path.

9. The circuit according to claim 1, further comprising a memory, the analog input signal generator is configures to retrieve waveform data from the memory.

10. The circuit according to claim 1, further comprising a lowpass filter that filters the measurement signal and the calibration signal prior to sampling.

* * * * *